United States Patent [19]

Anderson et al.

[11] 4,344,966
[45] Aug. 17, 1982

[54] ANTI-INFLAMMATORY 1-ALKYL-1-PHENYL-BUTANES

[75] Inventors: Paul L. Anderson, Dover, N.J.; Darryl A. Brittain, New York, N.Y.

[73] Assignee: Sandoz, Inc., E. Hanover, N.J.

[21] Appl. No.: 110,442

[22] Filed: Jan. 8, 1980

Related U.S. Application Data

[60] Continuation of Ser. No. 867,789, Jan. 9, 1978, abandoned, which is a division of Ser. No. 633,460, Nov. 19, 1975, Pat. No. 4,081,476, Continuation-in-part of Ser. No. 390,035, Aug. 20, 1973, abandoned.

[51] Int. Cl.$^3$ ............... A61K 31/065; A61K 31/085; A61K 31/22
[52] U.S. Cl. ................... 424/343; 424/311; 424/341; 560/255; 568/643; 568/809
[58] Field of Search ............ 568/807, 812, 813; 424/311, 340, 343, 341; 560/255

[56] References Cited

U.S. PATENT DOCUMENTS

| | | | |
|---|---|---|---|
| 3,859,256 | 1/1975 | Teufel et al. | 568/807 |
| 3,950,427 | 4/1976 | Engel et al. | 424/343 |
| 4,081,476 | 3/1978 | Anderson et al. | 568/807 |

OTHER PUBLICATIONS

Ribereau et al., *Bull. Soc. Chim. France,* (1972), pp. 1581–1587.

*Primary Examiner*—Natalie Trousof
*Assistant Examiner*—L. Hendriksen
*Attorney, Agent, or Firm*—Gerald D. Sharkin; Richard E. Vila; Frederick H. Weinfeldt

[57] ABSTRACT

The compounds are 1-aryl-1-lower alkyl-substituted-1-buten-3-ols, butan-3-ols, and acylation products thereof, e.g., (p-biphenylyl)-2-penten-4-ol and are useful as pharmaceuticals.

11 Claims, No Drawings

ANTI-INFLAMMATORY 1-ALKYL-1-PHENYL-BUTANES

This is a continuation of application Ser. No. 867,789, filed Jan. 9, 1978, now abandoned which in turn is a division of application Ser. No. 633,460, filed Nov. 19, 1975, now U.S. Pat. No. 4,081,476, which in turn is a continuation-in-part of Ser. No. 390,035, filed Aug. 20, 1973, now abandoned.

This invention relates to chemical compounds, and more particularly to 1-aryl-1-alkyl-substituted-butane and -1-butene alcohols and esters, and to the preparation of such compounds, as well as to pharmaceutical compositions containing such compounds and the use of such compounds.

The compounds of this invention may be conveniently represented by the formula I

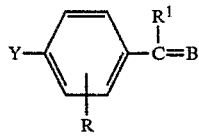

wherein
- $R^1$ is alkyl, having from 1 to 3 carbon atoms,
- R is a hydrogen atom, or halo having an atomic weight of from about 19 to 80, i.e., fluoro, chloro or bromo;
- Y is halo having an atomic weight of from about 80 to 127, i.e., bromo or iodo, isobutyl, tert.-butyl, cyclohexyl, cyclohex-1-enyl, or a radical of type (a):

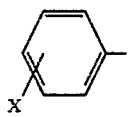

wherein
X is a hydrogen atom, or halo having an atomic weight of from about 19 to 80, or alkoxy having from 1 to 4 carbon atoms, (including isomeric forms where such exist); or
Y is a radical of type (b):

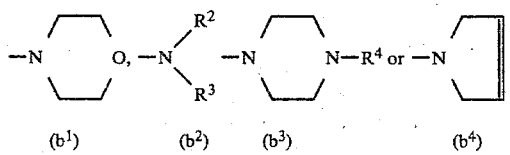

wherein each of
$R^2$ and $R^3$, independently, is alkyl having 1 to 3 carbon atoms, or $R^2$ and $R^3$ are joined to form with the nitrogen atom a pyrrolidino or piperidino ring, and
$R^4$ is a hydrogen atom or alkyl having 1 to 3 carbon atoms; and
B is either of the structures of type:

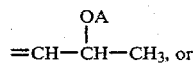

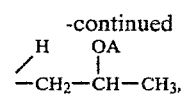

wherein
A is a hydrogen atom or lower alkanoyl, e.g., having from 2 to 4 carbon atoms, such as acetyl, propionyl or butyryl, or acetoacetyl.

The class of Compounds I may be viewed as including four sub-classes of compounds depending upon the nature of B; A, $R^1$, R and Y being as defined above, and A' representing A when it is other than a hydrogen atom, i.e., when A is lower alkanoyl or acetoacetyl:

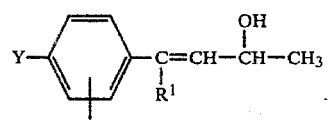

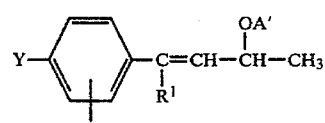

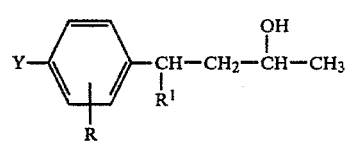

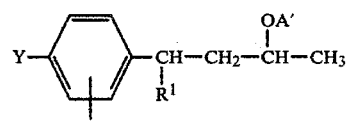

Compounds I may also be conveniently viewed as comprising two subclasses, i.e., Ia consisting of Ia1+Ia2 and Ib consisting of Ib1+Ib2.

Compounds Ia2 and Ib2, are acylated derivatives of compounds Ia1 and Ib1, respectively, obtainable by acylating Compounds Ia1 or Ib1 (process 1). Conversely, Compounds Ia1 and Ib1 may be obtained by saponification of the corresponding Compounds Ia2 and Ib2, respectively (process 2). Compounds I are thus interconvertible.

Compounds Ib1 are obtainable by reducing the unsaturation of a corresponding Compound Ia1 (process a).

Compounds Ia1 are obtainable by reducing (process b) the carbonyl function of a corresponding 4-aryl-4-alkyl-3-buten-2-one of the formula II:

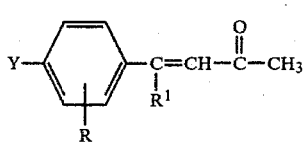

wherein R, $R^1$ and Y are as defined above.

Compounds II, in turn, are obtainable by aqueous acidic treatment (process c) of corresponding 1-aryl-1-alkyl-2,3-butadien-1-ols of the formula III:

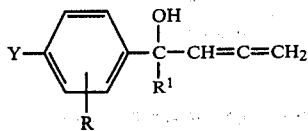

wherein R, R¹ and Y are as defined above.

The preparation of the various sub-classes comprising compounds I may be conveniently represented by Reaction Scheme A, below, wherein R¹ and A' are as defined above and Ph represents the substituted phenyl nucleus

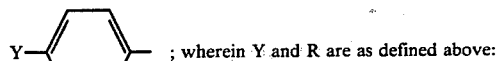

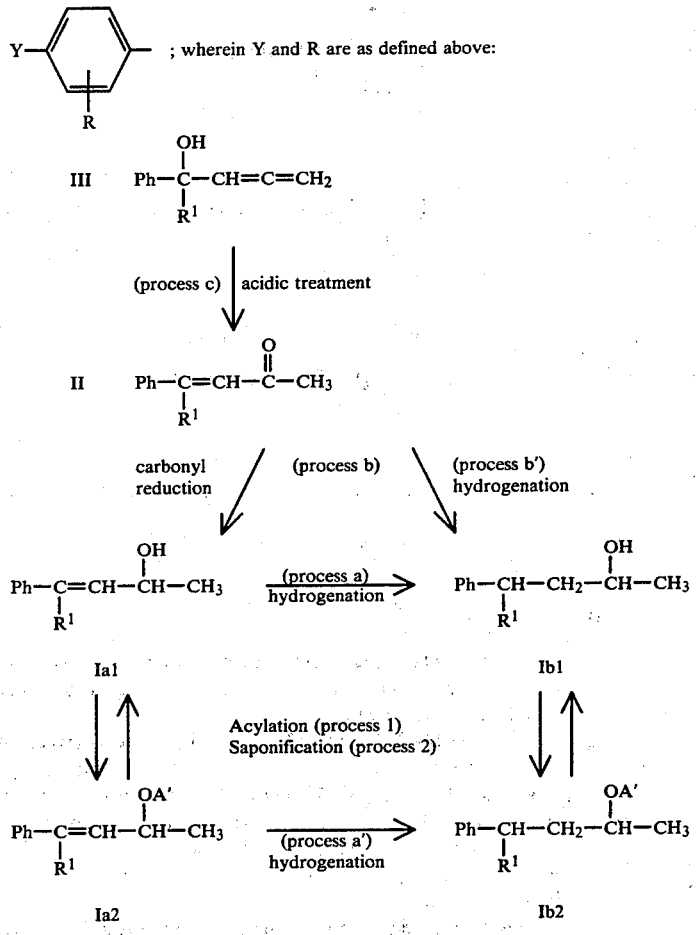

The acylation of compounds Ia1 or Ib1 (process 1); may be carried out by conventional techniques. The acylation, thus, may be effected by processes known per se for the acylation of secondary aliphatic alcohols. Suitable alkanoylating agents include organic acids, acyl halides and acid anhydrides of formulae Ac-OH, Ac-Hal and (Ac)₂O, respectively, wherein Ac is a lower alkanoyl group suitable as A when it is a lower alkanoyl group as defined above, and Hal signifies bromine or chlorine, and mixtures thereof. Where the desired alkanoyl moiety is acetyl, a preferred acylating agent is acetic anhydride. In carrying out the alkanoylation inert solvent may be employed or excess alkanoylating agent may serve as solvent. An acid binding agent, e.g., pyridine, is suitably used. Preferred temperatures vary between −10° and 50° C. If desired, more stringent conditions may be used, characterized by the presence of a strongly acidic catalyst, e.g., p-toluene-sulphonic acid. If such catalysts are used, in addition to the above-listed alkanoylating agents, enol acylates, preferably esters of "isopropenyl alcohol", e.g. isopropenyl acetate, may also be employed. The considerations involved are well within the scope of one skilled in the art. The formation of a acetoacetyloxy function may be carried out by reacting a compound Ia1 or Ib1 with diketene under conventional conditions for such a reaction. The process is suitably effected in an inert organic solvent, such as benzene, toluene or a mixture thereof, and in the presence of a small amount of an organic tertiary amine, e.g., pyridine. The process is conveniently carried out at a relatively low temperature, e.g., from −5° to +35° C.

The acylated forms of Compounds I, i.e., Compounds Ia2 and Ib2, may be saponified (process 2) employing conventional means, e.g., by treatment with dilute sodium hydroxide or or methanolic potassium bicarbonate, to obtain a corresponding hydroxy-bearing Compound I, i.e., Compounds Ia1 and Ib1.

Process (a) involves the reduction of the unsaturated position of a Compound Ia1 to obtain the corresponding Compound Ib1. The process may be carried out by treating a Compound Ia1 with hydrogen at moderate pressures, e.g., up to about 3 atmosphere. The process may be carried out in an inert solvent, e.g., a lower alkanol, such as methanol or ethanol, ethyl acetate, benzene, glyme, or dioxane, at moderate temperatures, e.g., from about −20° to +30° C., preferably at room temperature (20° to 30° C.), employing a conventional hydrogenation catalyst, e.g., 10% palladium on charcoal. Other catalysts such as palladium on an inert carrier such as barium carbonate, may similarly be used.

Process (b) involves reducing the carbonyl function of a Compound II to obtain the corresponding Compound Ia1. The reduction may be carried out using conventional techniques for the reduction of an aliphatic ketone to its corresponding alcohol. For example, a complex metal hydride, such as sodium aluminum diethyl dihydride or lithium aluminum tri-t-butoxy hydride may be employed in an aprotic medium, e.g., an ether, such as diethyl ether, tetrahydrofuran, or dioxane, or an aromatic medium, such as benzene or toluene under essentially anhydrous conditions. The medium may be a single material or a mixture. The reaction may be conveniently carried out at temperatures of from about −10° to 40° C., preferably at about −5° to +15° C.

Alternatively, subjecting a Compound II to the reducing conditions of process (a) yields the corresponding Compound Ib1 (process b'), thus by-passing process (b). Furthermore, if desired, a Compound Ia2 may be subjected to the reducing conditions of process (a) to obtain the corresponding Compound Ib2 (process a').

Process (c) involves aqueous acidic treatment of a Compound III to obtain the corresponding Compound II, and may be carried out employing as the "acidic" source a strong protonating agent, in a suitable medium, at moderate temperatures, e.g., 10° to 100°., preferably at 15° to 35° C. Where the protonating agent is liquid under the process conditions, it may be used in excess to serve as the medium, however, it is preferable to include a water-miscible solvent such as ethanol or methanol.

Suitable protonating agents include mineral acids, such a hydrochloric or hydrobromic, or sulfuric acid, and aromatic- or (lower) aliphatic sulfonic acids, such as p-toluenesulfonic acid. Process (c) may likewise be carried out using lower carboxylic acids, e.g., having from 1 to 3 carbon atoms, such as acetic acid, but more vigorous reaction conditions may then be necessary.

If hydrochloric (or hydrobromic) acid is employed as the acidic source in process (c), then in addition to the corresponding Compound II product, a corresponding 4-substituted-phenyl-4-alkyl-2-chloro-(or bromo)-1,3-butadiene co-product will also be formed. The products can be separated so as to recover the Compound II product, by conventional recovery procedures, such as fractional crystallization and chromatographic techniques.

The above-described intermediates Compounds II and III are either known compounds or analogs of known compounds and are obtainable by adaption of the methods described in the literature for the preparation of such compounds, e.g., Belgian Pat. No. 792,079, and West German DT No. 2,258,349 (Chemical Abstracts 79, 5287c).

The compounds of formula I exist as geometric isomers and may be produced in the form of pure cis- or trans- isomers or in the form of isomeric mixtures which may, if desired, be separated, in conventional manner, into individual isomers. The process (c) described above yields the compounds predominantly or substantially in trans-isomeric from but other isomeric forms or mixtures may, if desired, be produced in conventional manner, for example, by stereospecific synthesis or by "scrambling" the compounds obtained predominantly or substantially in trans-form as described above, e.g., by UV irradiation, and, if desired, separating the resulting isomeric mixtures using conventional techniques. Processes (b) and (e), described above, will yield the products in the same geometric form as the starting materials. In any event, while the compounds are preferably in pure trans-isomeric form or in the form of isomeric mixtures in which the trans-isomer predominates, e.g., to the extent of about 60 to 99%, preferably 70 to 99%, more preferably 80 to 99%, it is to be understood that the invention is not intended to be limited to any particular form of the compounds.

Compounds II may alternatively be prepared by process (3), by reacting an acyl halide, i.e., a compound of formula IV:

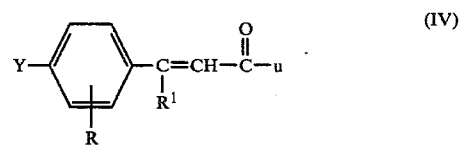

in which Y, R and $R^1$ are as defined and u is chloro or bromo, with a methyl-contributing organometallic reagent:

$CH_3$—k in which k is an equivalent of an active metal cation or magnesium bromide or iodide, in an aprotic medium which is not detrimental to the reaction and under anhydrous conditions; and hydrolyzing the resultant adduct.

Process (3) may be conveniently carried out in the conventional manner for carrying out a Grignard-type reaction. The k moiety of the organometallic reagent used may be an alkali metal, e.g., Li, however, the preferred organometallic reagents include Grignard reagents, such as methyl magnesium halides, particularly methyl magnesium bromide. Suitable aprotic media include ethers, such as tetrahydrofuran or diethyl ether, and the reaction is preferably carried out at reduced temperatures of, for example, −30° to 0° C. The subsequent hydrolysis may be carried out in conventional manner for hydrolyzing a Grignard-type adduct, for example, with an aqueous salt solution such as saturated ammonium chloride solution. When, in a compound of formula IV, Y is an unsubstituted piperazino radical, an additional equivalent of the organometallic reagent is preferably used.

The organometallic reagents employed in process (3), above, are either known or may be prepared in conventional manner from available materials; many being commercially available.

The compounds of formula IV may be produced by chlorinating or brominating a corresponding free acid of formula V:

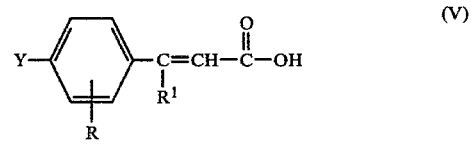

in which R, $R^1$ and are as defined above, in conventional manner, for example, at a temperature of from 30° to 120° C. Suitable chlorinating agents include phosphorus trichloride or, preferably, thionyl chloride, and suitable brominating agents include phosphorus tribromide. An inert solvent, e.g., tetrahydrofuran, may suitably be employed. Alternatively, an excess of the chlorinating or brominating agent may, where it is liquid under the reaction conditions, be used to provide a reaction medium.

The resulting compounds of formula IV may be isolated and purified using conventional techniques.

The compounds of a formula V may be produced by saponifying a compound of formula VI:

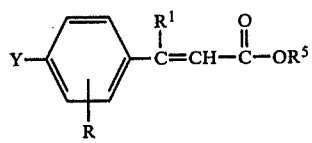

VI in which R, Y and $R^1$ are as defined above,
and $R^5$ is straight chain alkyl of 1 to 6 carbon atoms, preferably ethyl.

The process is suitably effected by heating the compound of formula VI, preferably at a temperature of from 70° to 120° C., in an aqueous solution of an alkali metal hydroxide, e.g. sodium hydroxide or potassium hydroxide. Preferably, the process is effected in the presence of a water-miscible co-solvent, such as an alkanol of 1 to 4 carbon atoms, e.g., ethanol or methanol.

The resulting compounds of formula V may be isolated and purified using conventional techniques.

The compounds of formula VI are either known or may be produced in conventional manner from available materials.

It should be noted that the compounds of formula II exist in the form of geometric isomers and the geometric form produced by process (3) depends on the configuration of the starting materials of formula IV. Thus, for example, the compounds of formula I may be obtained substantially or predominately in trans form by process (3) by using compounds of formula IV which are substantially or predominately in trans form. The compounds of formula IV may be obtained substantially or predominately in trans form by using, initially, compounds of formula VI which are substantially or predominately in trans form. The compounds of formula VI, substantially or predominately in trans form, may be produced directly by dehydrating a compound of formula VII:

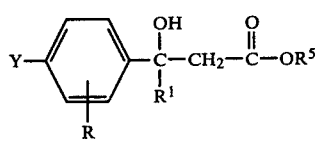

VII in which R, $R^1$, $R^5$ and Y are as defined above.

The process may be carried out by heating a compound of formula VII, suitably at a temperature of from 80° to 200° C., under vacuum, for example 0.01 to 0.5 mm of mercury.

The resulting products may be isolated and purified using conventional techniques.

Other isomeric forms of the compounds of formula VI, which would lead to the corresponding configuration in the final products of formula I, may be produced by conventional methods, for example by stereospecific synthesis from available materials, or by "scrambling" the compounds obtained predominately or substantially in trans form as described above, e.g. by UV irradiation, and, if desired, separating the resulting isomeric mixtures using conventional techniques.

It will be appreciated that particular forms of the compounds of formula II produced as described above, may themselves be "scrambled" and the resulting isomeric mixtures, if desired, separated by conventional techniques.

The compounds of formula VII are either known or may be produced in conventional manner from available materials. A preferred method for their production involves reaction of a compound of formula VIII:

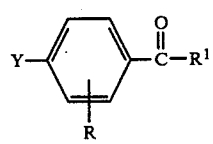

VIII in which R, $R^1$ and Y are as defined above, with a compound of formula IX:

$$ZnBrCH_2COR^5$$

IX in which $R^5$ is as defined above, in an aprotic solvent and under anhydrous conditions, and hydrolysing the resulting adduct.

Suitable solvents include ethers, such as tetrahydrofuran. Suitable reaction temperatures are moderate, for example from 15° to 30° C.

The subsequent hydrolysis may suitably be carried out using water, an aqueous acid base, or an aqueous solution of a salt, e.g., concentrated ammonium hydroxide or dilute sulphuric acid.

The compounds of formula IX may be produced, conveniently in situ, by heating activated zinc, preferably finely divided, e.g., 20 mesh, with $R^5$-bromoacetate in an aprotic solvent, e.g., tetrahydrofuran. The process is, preferably, carried out in the presence of trimethyl borate. The treatment is suitably effected at a temperature of from 15° to 30° C. When trimethyl borate is used in the in situ preparation of a compound IX, it is convenient to include in the hydrolysis step, when using an aqueous base, in addition, glycerine.

The resulting compounds of formula VII may be isolated and purified using conventional techniques.

Compounds VIII and IX are either known or may be prepared in conventional manner from available materials, and many are commercially available.

An alternative method of preparing Compounds Ial involves reacting (process 4) an aldehyde, i.e., a compound of the formula XI,

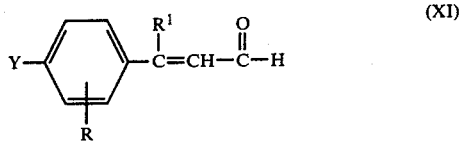

(XI)

in which R, $R^1$ and Y are as defined above, with an organmetallic reagent:

CH₃—k in which k is as defined above, in an aprotic medium (which is not detrimental to the reaction), and hydrolyzing the resulting adduct, e.g., in the conventional manner for hydrolyzing Grignard adducts, as described above.

in process (4), the reaction between the reagent and a compound XI is preferably carried out in a manner conventional for Grignard reactions, for example, in such aprotic media as ethers, e.g., diethyl ether. The reaction is preferably effected under anhydrous condition and, suitably, at a reduced temperature, e.g., $-50°$ to $+20°$ C., preferably $0°$ to $10°$ C. The subsequent hydrolysis may suitably be effected with water, an aqueous acid or base, or an aqueous solution of a salt, preferably with saturated aqueous ammonium chloride. When, in a compound of formula XI, Y is an unsubstituted piperazino radical, an additional equivalent of the organometallic reagent is preferably used. A preferred organometallic reagent is:

CH₃—MgBr

The resulting compounds of formula Ial may be isolated and purified using conventional techniques. Where desired free base forms of the compounds of formula XI in which Y is a radical of type $b^1$, $b^2$, $b^3$ or $b^4$, may be converted into acid addition salt forms in conventional manner, and vice versa. Suitable acids for salt formation include mineral acids such as hydrochloric acid.

The compounds of formula XI, employed as intermediates in process (4), may be produced by reducing a corresponding compound of formula IV, e.g., with lithium tri-t-butoxyaluminium hydride.

The reduction is suitably carried out at a temperature of from $-80°$ to $-60°$ C., preferably $-75°$ to $-78°$ C., conveniently in an inert organic solvent, preferably diglyme, and, under essentially anhydrous conditions.

The resulting compounds of formula XI may be isolated and purified using conventional techniques.

The above-described alternative processes and associated processes are conveniently represented by Reaction Scheme B, below in which Ph, $R^1$, $R^5$, u and k are as defined above:

REACTION SCHEME B

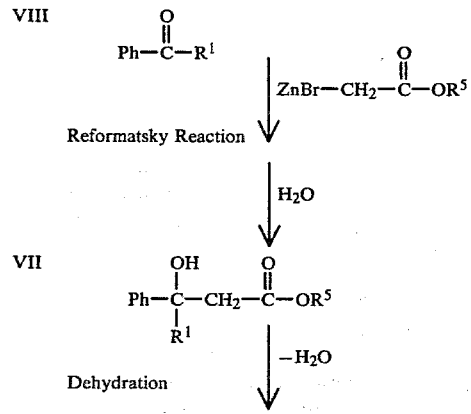

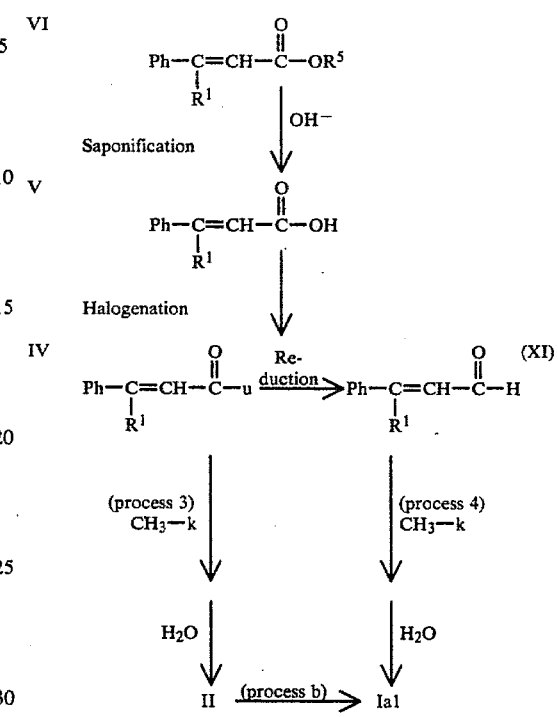

It will be noted that within each of the subclasses Ia and Ib of this invention further subdivisions are comprehended, e.g., compounds in which R is either a hydrogen atom or a substituent; B is either of the type (a) or (b); and Y is (1) amino (i.e. of type b); (2) halo (i.e. Y=Br or I), or (3) hydrocarbyl; the hydrocarbyl subdivision consisting of 2 groups, i.e., aryl, (of type a), and alkyl (which group may be still further subdivided into acyclic, i.e., isobutyl and t-butyl, and cyclic, i.e., cyclohexyl and cyclohexenyl radicals). The amino radicals are of heterocyclic ($b^1$, $b^3$ and $b^4$) and nonheterocyclic types ($b^2$). Compounds Ia and Ib are also comprehended in which when Y=type (a) the aryl radical may be unsubstituted (X=H), or substituted (X≠H) and X may be at the ortho-, meta-, or para-positions.

In any reaction described herein where essentially anhydrous conditions are involved, such may be achieved by means conventionally practiced where it is desired to essentially exclude moisture, e.g., by the use of absolute (anhydrous) reaction media and reagents, employing moisture-free apparatus and excluding moisture-laden air.

The products of the above-described reactions may be recovered and refined in conventional manner, e.g., by crystallization, distillation or chromatographic techniques, such as eluting from a chromotographic column or separating on a silica layer.

STATEMENT OF UTILITY

The compounds of formula I are useful because they possess pharmacological activity in animals. In particular, the compounds I are useful as anti-inflammatory agents as indicated by the Carrageenan induced edema test on rats (oral administration at 5 to 200 mg./kg.). For such use, the compounds may be combined with a pharmaceutically acceptable carrier, and such other conventional adjuvants as may be necessary, and administered orally in such forms as tablets, capsules, elixirs, suspensions and the like or parenterally in the form of an injectable solution or suspension. The dosage administered will, of course, vary depending upon the compounds used and the mode of administration. However, in general, satisfactory results are obtained when administered at a daily dosage of from about 1 milligram to about 200 milligrams per kilogram of body weight, preferably given in divided doses 2 to 4 times a day, or in sustained release form. For most mammals the administration of from about 70 milligrams to about 1500 milligrams of the compound per day provides satisfactory results and dosage forms suitable for internal administration comprise from about 20 milligrams to about 800 milligrams of the compound in admixture with a solid or liquid pharmaceutical carrier or diluent, e.g., a sterile suspension or a solid composition, comprising, for example, from about 5 to 95% of a compound I, e.g., from about 5% to 50% of a compound I.

As noted above, oral administration with carriers may take place in such conventional forms as tablets, dispersible powders, granules, capsules, syrups and elixirs. Such compositions may be prepared according to any method known in the art for manufacture of pharmaceutical compositions, and such compositions may contain one or more conventional adjuvants, such as sweetening agents, flavoring agents, coloring agents and preserving agents, in order to provide an elegant and palatable preparation. Tablets may contain the active ingredient in admixture with conventional pharmaceutical excipients, e.g., inert diluents such as calcium carbonate, sodium carbonate, lactose and talc, granulating and disintegrating agents, e.g., starch and alginic acid, binding agents, e.g., starch, gelatin and acacia, and lubricating agents, e.g., magnesium stearate, stearic acid and talc. The tablets may be uncoated or coated by known techniques to delay disintegration and absorption in the gastro-intestinal tract and thereby provide a sustained action over a longer period. Similarly, suspensions containing, for example, from about 0.5 to 5% of suspending agent, syrups containing, for example, from about 10 to 50% of sugar, and elixirs containing, for example, from about 20 to 50% of ethanol may contain the active ingredient in admixture with any of the conventional excipients utilized for the preparation of such compositions, e.g., suspending agents (methylcellulose, tragacanth and sodium alginate), wetting agents (lecithin, polyoxyethylene stearate and polyoxyethylene sorbitan monoleate) and preservatives (ethyl-p-hydroxybenzoate). Capsules preferably contain the active ingredient admixed with an inert diluent, e.g., a solid diluent such as calcium carbonate, calcium phosphate and kaolin or a liquid diluent, such as polyethylene glycol or an edible oil, e.g., peanut, corn or sesame oil. The preferred pharmaceutical compositions from the standpoint of preparation and ease of administration are orally administrable compositions, particularly tablets and solid or liquid diluent-filled capsules.

When the substituent Y is a radical of structures $b^1$, $b^2$, $b^3$ or $b^4$ then such compounds I may be similarly administered in the form of their nontoxic pharmaceutically acceptable acid addition salts. Such salts do not materially differ from the free base in their pharmacological effects and are included within the scope of the invention. The acid addition salts are readily prepared by reacting the base with pharmacologically acceptable acids in conventional manner. Representative of such salts are the mineral acid salts such as the hydrochloride, hydrobromide, sulfate, phosphate and the like and the organic salts such as the benzoate, acetate, maleate, p-toluenesulfonate, benzenesulfonate and the like.

In the following examples, which illustrate the invention, temperatures are in degrees centigrade, and room temperature is 20° to 30° C., unless indicated otherwise. Olefinic products are understood to be in substantially trans form, unless indicated otherwise. Trans forms are understood to be those in which the olefinic hydrogen atom and $R^1$ are on opposite sides of the double bond.

EXAMPLE 1

2-(p-Biphenylyl)-2-penten-4-ol

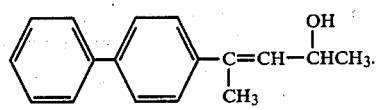

Step A: 2-(p-Biphenylyl)-2-penten-4-one.

To a solution of 10 g. of 2-(p-biphenylyl)-3,4-pentadien-2-ol in 200 ml. of anhydrous methanol is added 3 ml. of concentrated hydrochloric acid (12 N). The resulting mixture is stirred at room temperaure for 3 hours and then in an ice bath for 2 hours. Solids formed are filtered off and recrystallized from pentane to obtain 2-(p-biphenylyl)-2-penten-4-one, m.p. 130°–133° C. 2-(p-(biphenylyl)-4-chloro-2,4-pentadiene, byproduct, remains in the mother liquor.

Step B: 2-(p-Biphenylyl)-2-penten-4-ol.

To a solution of 1.6 g. 2-(p-biphenylyl)-2-penten-4-one in 25 ml. of dry tetrahydrofuran, at 0° C., 10 ml. of a solution of 25% (W/W) of sodium aluminum diethyl dihydride in toluene is dropwise added. After 20 minutes at 0° C., the mixture is poured onto ice and extracted with chloroform. Evaporation of the chloroform gives 2-(p-biphenylyl)-2-penten-4-ol, m.p. 137°–138° C.

EXAMPLE 2

2-(p-Biphenylyl)-pentan-4-ol

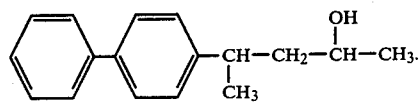

To a pressure vessel, mixture of 0.675 g. of 2-(p-biphenylyl)-2-penten-4-ol (obtainable by Example 1) and 0.5 g. 10% palladium on carbon in 175 ml. of ethanol, is added hydrogen at about 2 at. pressure via below pressure hydrogenation. The catalyst is then removed, and the solution is evaporated to give a colorless oil which solidifies on standing to give solid 2-(p-biphenylyl)-pentan-4-ol, m.p. 53° C., which may also be designated 4-(p-biphenylyl)-pentan-2-ol.

Repeating the procedures of Example 1 and of this example, but using in place of the 2-(p-biphenylyl)-3,4-pentadien-2-ol (of Example 1), an equivalent amount of the compound of column (A) there is similarly obtained the compounds of columns (B) and (C):

|   | A | B | C |
|---|---|---|---|
| a) | 2-(p-tert.butyl-phenyl)-3,4-pentadien-2-ol | 2-(p-tert.butyl-phenyl)-2-penten-4-ol | 4-(p-tert.butyl-phenyl)-pentan-2-ol |
| b) | 2-(p-bromophenyl)-3,4-pentadien-2-ol | 2-(p-bromophenyl)-2-penten-4-ol | 4-(p-bromophenyl)-pentan-2-ol |
| c) | 2-(p-cyclohexyl-m-chlorophenyl)-3,4-pentadien-2-ol | 2-(p-cyclohexyl-m-chlorophenyl)-2-penten-4-ol | 4-(p-cyclohexyl-m-chlorophenyl)-pentan-2-ol |
| d) | 2-(p-isobutyl-phenyl)-3,4-pentadien-2-ol | 2-(p-isobutyl-phenyl)-2-penten-4-ol | 4-(p-isobutyl-phenyl)-pentan-2-ol |
| e) | 2-(p-biphenylyl)-3,4-heptadien-2-ol | 4-(p-biphenylyl)-3-hepten-2-ol | 4-(p-biphenylyl)-heptan-2-ol |
| f) | 2-(p-1'-cyclohexenylphenyl)-3,4-pentadien-2-ol | 2-(p-1'-cyclohexenylphenyl)-2-penten-4-ol | 4-(p-1'-cyclohexenylphenyl)-pentan-2-ol |
| g) | 2-(p-morpholino-phenyl)-3,4-pentadien-2-ol | 2-(p-morpholino-phenyl)-2-penten-4-ol hydrochloride | 4-(p-morpholino-phenyl)-pentan-2-ol hydrochloride |
| h) | 2-[p-(N-methyl-piperazinyl)phenyl]-3,4-pentadien-2-ol | 2-[p-(N-methyl-piperazinyl)phenyl]-2-penten-4-ol hydrochloride | 4-[p-(N-methyl-piperazinyl)phenyl]-pentan-2-ol hydrochloride |
| i) | 2-(p-3-pyrrolinyl-phenyl)-3,4-pentadien-2-ol | 2-(p-3-pyrrolinyl-phenyl)-2-penten-4-ol hydrochloride | 4-(p-3-pyrrolinyl-phenyl)-pentan-2-ol hydrochloride |

EXAMPLE 3

4-Acetoxy-2-(p-biphenylyl)-2-pentene.

To a solution of 0.9 g. of 2-(p-biphenylyl)-2-penten-4-ol (obtainable by Example 1) in 75 ml. of dry pyridine, 10 ml. of acetic anhydride is added. After 18 hours at room temperature, the mixture is poured onto ice and the solids filtered off and recrystallized from pentane to give 4-acetoxy-2-(4-biphenylyl)-2-pentene, m.p. 62°–64° C., which may also be designated 4-(p-biphenylyl)-penten-2-ol acetate.

Repeating the procedure of this example using in place of the 2-(p-biphenylyl)-2-penten-4-ol an equivalent amount of the compounds listed below, there is similarly obtained the acetates thereof:

(a) 2-(p-bromophenyl)-2-penten-4-ol, (b) 4-(p-isobutyl-phenyl)-pentan-2-ol, (c) 2-(p-cyclohexyl-m-chlorophenyl)-2-penten-4-ol, and (d) 2-(p-biphenylyl)-pentan-4-ol.

EXAMPLE 4

Repeating the procedure of Example 1, but using as starting materials in place of the 2-(p-biphenylyl)-3,4-pentadien-2-ol an approximately equivalent amount of:

(a) 2-(p-cyclohexylphenyl)-3,4-pentadien-2-ol; or (b) 3-(p-biphenylyl)-4,5-hexadiene-3-ol; there is accordingly obtained:

(a) 4-(p-cyclohexylphenyl)-3-penten-2-ol, m.p. 73°–74°; and (b) 4-(p-biphenylyl)-3-hexen-2-ol, m.p. 73°–74°.

EXAMPLE 5

2-(p-Biphenylyl)-2-penten-4-ol (alternative process)

(a) 3-(4-Biphenylyl)-2-butenoic acid ethyl ester 6.45 g (0.1 mole) of activated zinc metal (20 mesh) is placed in a flask fitted with a septum inlet and a magnetic stirrer. The system is maintained under a nitrogen atmosphere and kept at a temperature of 25° C. on a water bath. A solution of 19.6 g (0.1 mole) of 4-acetyl-biphenyl in 75 ml of dry tetrahydrofuran and 75 ml of trimethyl borate (distilled from calcium hydride) is injected and the mixture stirred. 11.1 ml (0.1 mole) of freshly distilled ethyl bromoacetate is injected in one shot and the mixture stirred at 25° C. for 12 hours. A mixture of 25 ml of concentrated ammonium hydroxide and 75 ml of glycerine is added, and the aqueous phase is separated and extracted thrice with 25 ml portions of diethyl ether. The combined organic extracts are dried over anhydrous magnesium sulphate and the diethylether removed on a rotary evaporator, the residue is vacuum distilled and the fraction distilling at 0.125 mn at 171°–172° C. is collected. Recrystallisation from petroleum ether yields the heading compound, substantially in trans form.

(b) 3-(4-Biphenylyl)-2-butenoic acid

The product resulting from (a), above, is mixed with 6 g of 85% potassium hydroxide in 100 ml of aqueous ethanol and the resulting mixture heated on a steam bath for 30 minutes. The mixture is then cooled, poured into ice and extracted thrice with 25 ml portions of diethylether. The aqueous phase is filtered over Celite and the filtrate acidified with 2 N hydrochloric acid to pH 4 and cooled. The resulting precipitate is filtered, washed with ether, air dried with suction and then dried under high vacuum at 50° C. to yield the heading compound, substantially in trans form.

(c) 3-(4-Biphenylyl)-2-butenoic acid chloride

The crude product, resulting from (b), above, is dissolved in 200 ml of dry tetrahydrofuran and 4 ml (0.055 mole) of thionyl chloride is added. The solution is refluxed under a nitrogen atmosphere for 3 hours and the solvent and excess thionyl chloride then distilled off. The resulting residue is flash distilled in a microdistillation apparatus at 145°–153° C. and 0.075 mm to yield the heading compound, substantially in trans form.

(d) 3-(4-Biphenylyl)-2-butenaldehyde (i) To 5.4 g (0.142 mole) of lithium aluminium hydride in 200 ml of diethylether is added, dropwise, t-butanol until hydrogen evolution ceases. The ether and t-butanol are then removed under vacuum and the solids dissolved in 300 ml of anhydrous diglyme to yield lithium tri-t-butoxy aluminium hydride reagent.

(ii) The crude product from (c) above is dissolved in 200 ml of anhydrous diglyme and the solution cooled to −78° C. in a dry-acetone bath. The above reagent is similarly cooled and added, dropwise, over a period of 30 minutes. The mixture is then stirred for 2 hours while being allowed to warm to room temperature. The mixture is then poured into 1000 g of ice and the resulting solid collected on a filter and extracted with four 200 ml portions of 95% ethanol. The combined extracts are evapourated in vacuo and the resulting oil dissolved in diethyl ether. The solution is dried over anhydrous magnesium sulphate and evapourated in vacuo to yield an oil which solidifies as standing, this being the heading compound, substantially in trans form.

(e) 2-(p-Biphenylyl)-2-penten-4-ol

In a 500 ml three-necked flask equipped with a mercury-sealed stirrer, a reflux condenser protected with a calcium chloride drying tube, a separating funnel, a nitrogen inlet tube and a thermometer, is placed 0.1 mole of methyl magnesium bromide in 150 ml of anhydrous diethyl ether. The mixture is cooled to a temperature below 10° C. in an ice-water bath and 20 g (0.0895 mole) of the crude product of (d), above, dissolved in 75 ml of anhydrous diethyl ether, is added, at such a rate that the temperature does not exceed 10° C. Throughout the addition, which takes about 30 minutes, a slow stream of dry nitrogen is passed through the flask. The solution is then stirred for 30 minutes and 75 ml of saturated ammonium chloride solution (neutralised to litmus with concentrated ammonium hydroxide) is added, dropwise, the temperature being maintained at 5°–10° C. This addition takes 20 minutes and the ether layer is then decanted off, and the residual precipitate extracted with two 30 ml portions of absolute diethylether. The extracts are added to the decanted ether layer and the combined solution is then dried over anhydrous potassium carbonate. The solvent is then removed under vacuum and resulting oil is cooled in an ice bath to yield the crude product which is recrystallised from diethyl ether to yield the heading compound, mp 137°–138° C., substantially in trans form.

EXAMPLE 6

In manner analogous to Example 5, but employing appropriate starting materials in approximately equivalent amounts, the products of Examples 2 (column B) and 4 may be obtained.

EXAMPLE 7

2-(p-biphenylyl-2-penten-4-one (a compound II)

10.0 g. (0.039 mole) of crude acid chloride from Example 5, Step c, is dissolved in 200 ml. of dry tetrahydrofuran and the solution placed in a 500 ml. round bottom flask fitted with a septum inlet and magnetic stirrer, and held under a nitrogen atmosphere. The solution is cooled to −30° C. in a dry ice/isopropanol bath and 19.5 ml (0.039 mole) of a commercial 2 M methyl magnesium bromide solution in dry toluene is added, dropwise, over 30 minutes. After the addition is complete, the mixture is allowed to warm to room temperature and then stirred for 1 hour. The reaction is quenched by the addition of 20 ml. of saturated ammonium chloride solution and the organic layer is separated. The aqueous layer is extracted twice with 20 ml. portions of ether and the combined organic extracts are then dried over anhydrous magnesium sulphate and evaporated to yield the heading compound, m.p. 130° to 133° C., after recrystallization from petroleum ether.

EXAMPLE 8

In manner analogous to Example 7, above, but employing appropriate starting materials in approximately equivalent amounts, the compounds II corresponding to the products of Examples (2a), (b), (c), (d), (e), (f), (g), (h) and (i) may be obtained.

EXAMPLE 9

Tablets and capsules containing the ingredients indicated below may be prepared by conventional techniques and are useful in treating inflammation in mammals at a dose one tablet or capsule 2 to 4 times per day:

| Ingredient | Weight (in mg.) Tablet | Capsule |
|---|---|---|
| 2-(p-biphenylyl)-2-penten-4-ol(trans) | 50 | 50 |
| Tragacanth | 10 | |
| Lactose | 197.5 | 250 |
| Corn Starch | 25 | |
| Talcum | 15 | |
| Magnesium Stearate | 2.5 | |

What is claimed is:

1. A pharmaceutical composition suitable for use as an anti-inflammatory comprising a compound of the formula:

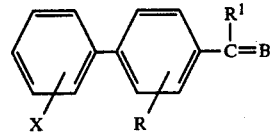

wherein
X is a hydrogen atom; halo having an atomic weight of from about 19 to 80, or alkoxy having from 1 to 4 carbon atoms;
R is a hydrogen atom or halo having an atomic weight of from about 19 to 80;
$R^1$ is alkyl having from 1 to 3 carbon atoms; and
B is either of the structures:

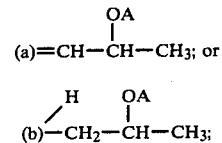

in which
A is a hydrogen atom or alkanoyl having from 2 to 4 carbon atoms, or acetoacetyl;
and a pharmaceutically acceptable carrier for said compound.

2. A composition of claim 1 in unit dose form suitable for oral administration in which the compound is present in an amount of about 20 milligrams to about 800 milligrams.

3. A composition of claim 1 in which the carrier is solid.

4. A composition of claim 1 which is a tablet or capsule.

5. A composition of claim 1 in which the compound is 2-(p-biphenylyl)-2-penten-4-ol (trans).

6. A pharmaceutical composition according to claim 1 suitable for use as an anti-inflammatory comprising a compound of the formula:

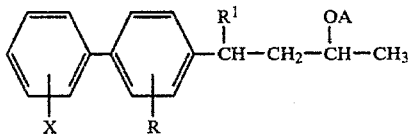

wherein

X is a hydrogen atom; halo having an atomic weight of from about 19 to 80, or alkoxy having from 1 to 4 carbon atoms;

R is a hydrogen atom or halo having an atomic weight of from about 19 to 80;

$R^1$ is alkyl having from 1 to 3 carbon atoms; and

A is a hydrogen atom or alkanoyl having from 2 to 4 carbon atoms, or acetoacetyl.

7. A method of treating inflammation in an animal in need of such treatment, comprising internally administering to said animal an inflammation-reducing amount of a compound of the formula:

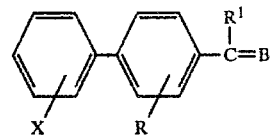

wherein

X is a hydrogen atom, halo having an atomic weight of from about 19 to 80; or alkoxy having from 1 to 4 carbon atoms;

R is a hydrogen atom or halo having an atomic weight of from about 19 to 80;

$R^1$ is alkyl having from 1 to 3 carbon atoms; and

B is either of the structures:

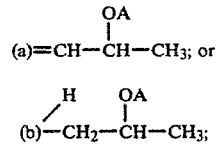

in which A is a hydrogen atom or alkanoyl having from 2 to 4 carbon atoms, or acetoacetyl.

8. A method of claim 7 in which the daily dosage of the compound is from about 70 milligrams to about 1500 milligrams.

9. A method of claim 7 in which the compound is 2-(p-biphenylyl)-2-penten-4-ol (trans).

10. A method of claim 7 in which the compound is one wherein A is a hydrogen atom and B is of type (a).

11. A composition of claim 1 in which the compound is one wherein A is a hydrogen atom and B is of type (a).

* * * * *